United States Patent [19]
Gilbert

[11] Patent Number: 5,161,523
[45] Date of Patent: Nov. 10, 1992

[54] RESUSCITATION MASK

[76] Inventor: James M. Gilbert, Rte. 1, Box 77-D, Concord, Va. 24538

[21] Appl. No.: 680,764

[22] Filed: Apr. 5, 1991

[51] Int. Cl.$^5$ ............................................. A61M 16/00
[52] U.S. Cl. ........................... 128/202.28; 128/205.29; 128/206.12
[58] Field of Search ....................... 128/202.28, 202.29, 128/205.29, 206.12, 206.14

[56] References Cited

U.S. PATENT DOCUMENTS

| | | | |
|---|---|---|---|
| 2,928,388 | 4/1957 | Jaroslaw | 128/206.14 |
| 4,004,584 | 1/1977 | Geaney | 128/206.14 |
| 4,382,440 | 5/1983 | Kapp | 128/201.25 |
| 4,467,799 | 8/1984 | Steinberg | 128/206.14 |
| 4,909,245 | 3/1990 | Wollenhaupt | 128/203.11 |

Primary Examiner—Edgar S. Burr
Assistant Examiner—Eric P. Raciti
Attorney, Agent, or Firm—Watson, Cole, Grindle & Watson

[57] ABSTRACT

A mask adapted to be placed over the mouth of a subject during mouth-to-mouth resuscitation includes a fibrous, central, air-permeable filter portion, a transparent portion surrounding the filter portion, and a stiffening portion surrounding the transparent portion, so that the mask may be grasped by the stiffening portion and visually adjusted through the transparent portion to locate the filter portion over the mouth of the subject.

11 Claims, 1 Drawing Sheet

RESUSCITATION MASK

FIELD OF THE INVENTION

The present invention relates generally to masks, and more particularly to a mask specifically adapted to be placed over the mouth of a person who requires aid in breathing, which aid is to be furnished by another person through what is referred to as mouth-to-mouth resuscitation.

BACKGROUND OF THE INVENTION

Mouth-to-mouth resuscitation has become a preferred form of inducing one whose air passages to the lungs have become fully or partially obstructed, being deemed more efficacious than other forms of artificial respiration. When one's breathing has stopped or is no longer apparent, regardless of other injuries that may have been suffered it is necessary that breathing be restored at once. If cessation of breathing lasts longer than several minutes, irreversible brain damage will be the result. Thus resuscitation in the form of mouth-to-mouth breathing assistance will often save the life of a victim of an accident or other trauma and, minimally, will prevent the victim from suffering brain damage.

Particularly with the advent of the AIDS disease, one administering mouth-to-mouth resuscitation to a stranger will have a well-justified apprehension that, by bringing his mouth into direct contact with that of the victim, he will be incurring the possibility of acquiring the HIV virus from the victim to himself by transfer of saliva and other mouth fluids. Moreover, when one is the victim, there is always the chance that, when unconscious, a well-meaning stranger who applies mouth-to-mouth resuscitation will unwittingly transfer the HIV virus from that resuscitator to the victim. It is, therefore, highly advisable that there be some means for preventing the transfer of communicable diseases between resuscitator and victim when mouth-to-mouth breathing restoration is supplied.

In one disclosure that has attempted to meet this problem, U.S. Pat. No. 4,510,931, a sanitary barrier is disclosed in a form of a sheet of expanded, porous polytetraflouroethylene bonded to a substrate. The opaque sheet of plastic is placed over the mouth of the victim and, according to the patentee, substantially prevents the transfer of aerosols, bacteria, particles and viruses between the practitioner and the patient.

However, it will be apparent that when placing any opaque sheet of material over the mouth of a victim, the mouth and the lower portion of the victim's face will be covered by the sheet, making it difficult to locate the mouth of the victim. In addition, since the mouth of the victim must be open in order to permit the passage of air into and from the victim's mouth, the use of an opaque sheet between the mouth of the victim and that of the resuscitator will prevent the resuscitator from observing whether the mouth of the victim has remained open and whether, in applying his own mouth to that of the victim, contact has been made in such a manner that air from the lungs of the resuscitator may be supplied fully and accurately through the open mouth of the victim. Even if resuscitation has commenced with the proper placement of the mouth of the resuscitator over that of the victim, a shifting of the position of the victim may result in the victim's mouth being displaced or closed. The resuscitator may then be unaware that while he is supplying air to the victim with a velocity that he deems appropriate given the body weight of the victim, that supply of air is inappropriate because some of the air passes out of the victim's mouth through a side thereof rather than being forced into his lungs.

As a consequence, it is a primary object of the present invention to provide an article of manufacture which will effectively separate the mouths of the victim and resuscitator during artificial respiration, but which will permit the resuscitator to view the mouth of the victim during that procedure. In this manner, the resuscitator will be able initially to position his mouth properly over the mouth of the victim so that air from the resuscitator will be supplied directly to the victim's air passageways, and such position may be maintained so that despite a shifting of the position of the mouth of the victim, the resuscitator can likewise shift the mask and/or his oral position and thereby continue effectively to revive the victim.

It is another object of the present invention to provide a mask that will have substance, i.e., a degree of stiffness and firmness so that it will tend to maintain the position in which it is placed. Also, it may be grasped by one hand of the resuscitator and maintained in operable position by virtue of its stiffness although grasped only at one end thereof. This is important because in modern resuscitation techniques one hand of the resuscitator is applied over the nose of the victim to close off the nasal passageway and prevent the escape therethrough of breath supplied during the procedure. Where a relatively soft, flexible sheet of material that does not have the requisite firmness is positioned over the mouth of the victim, such position will be difficult to maintain because a limp sheet of plastic will tend to shift position with repositioning of the victim's head unless constantly held at two locations. On the other hand, a firm mask can be grasped at one end and the entirety of the mask properly located over the victim's mouth by manipulating from that location, or it may retain its position without the need for any manual control whatsoever.

SUMMARY OF THE INVENTION

In accordance with the above objects, my invention takes the form of a mask adapted to be placed over the mouth of a victim during mouth-to-mouth resuscitation. It comprises an air-permeable filter portion which inhibits the passage of unsanitary materials therethrough but permits the breath of the resuscitator to pass quite freely. A transparent portion surrounds the filter portion, and a stiffening portion is in contact with and maintains the shape of the transparent portion and the filter portion of the mask during use thereof. In this manner the mask may be grasped by the stiffening portion and adjusted visually through the transparent portion to locate the filter portion of the mask over the mouth of the victim.

The precise form and construction of the mask may take many forms. Thus, the filter portion in one embodiment of my invention is a dry air filter. It may be composed of a material such as cotton, cellulose paper, glass fibers or various synthetic materials. In another form it may be an impingement filter in which at least one surface of the filter portion has an adhesive spray applied thereto. The spray may take the form of an antiseptic. In such an impingement filter, particles of the unsanitary materials will adhere to the fluid that has been applied to the filter portion.

With regard to the transparent portion of the mask, that portion is most advantageously formed from synthetic plastic film, for example, vinyl resin or polyvinylidene chloride, the latter being known by the trademark, SARAN. Certain synthetic polyester resins are also well adapted for this purpose.

The stiffening portion of the mask may or may not be opaque to the passage of light therethrough. If it is to be translucent or transparent, the stiffening portion may be formed from celluloid or an organic ester of cellulose.

In another embodiment of my invention, the transparent portion and stiffening portion are combined into a single portion. In this two-portion mask, the filter portion which inhibits passage of unsanitary materials therethrough but permits the breath of the resuscitator to pass readily is maintained. This portion is surrounded by a transparent portion that has a stiffness sufficient to permit it to be grasped by the user and accurately positioned over the mouth of the victim. Yet the portion will be sufficiently transparent or translucent in order that the proper positioning of the filter portion may be accomplished with visual accuracy. Since in this embodiment it is necessary that the stiffening member be translucent or transparent, that member will advantageously be formed from a translucent or transparent ester of cellulose or, conventionally, celluloid.

The foregoing objects and features of the present invention will be more apparent when considered in connection with preferred embodiments of my invention as illustrated in the accompanying drawings, in which.

DESCRIPTION OF PREFERRED EMBODIMENTS

Figure 1:
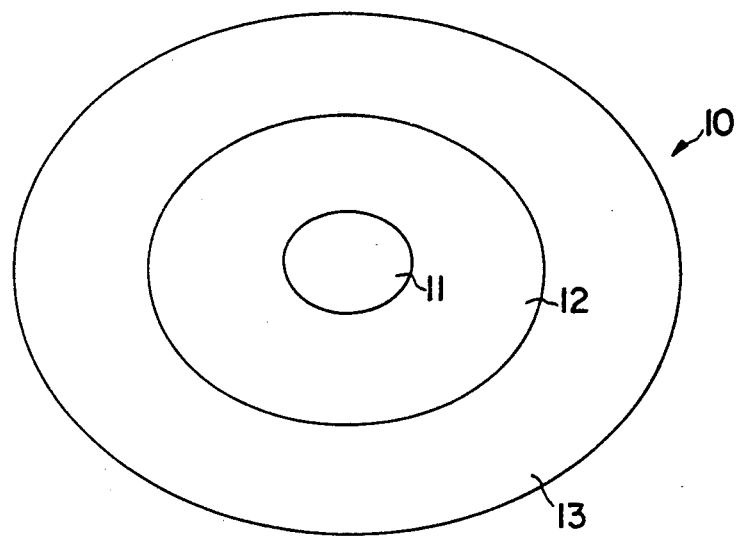
FIG. 1 is a plan view of a preferred, three-part mask.

Referring now to the embodiment of the invention shown in FIG. 1 of the drawing, what is there illustrated is what I presently consider to be the best mode of my invention. The mask 10 of FIG. 1 consists of three discrete portions: a central filter portion 11 adapted to be located over the mouth of the victim during mouth-to-mouth resuscitation; a transparent portion 12 which surrounds the central portion 11, and an exterior portion 13, which is joined to the transparent portion and which is adapted to be grasped manually in order to locate central filter portion 11 over the mouth of the victim. As shown, portions 12 and 13 are generally oblong in shape, although they obviously can take other forms. Filter portion 11 is substantially round.

With respect to the central portion 11, it is preferred that it be fibrous, and most preferably formed from cellulosic material. As shown, the central portion 11 is a dry air filter made of cellulose paper. In this form it is air-permeable, which is a requisite since the person performing the resuscitation will have to place his mouth over the central portion 11 and blow through it. While cellulose paper is the most preferred material from which the central portion 11 may be formed, it will be apparent that other materials can be used, e.g., cotton, glass fibers and other synthetic materials. In addition, the air filter can be what is known as a viscous impingement filter, in which at least one surface portion is coated with a liquid, such as an antiseptic solution. The presence of such a liquid, particularly if it has adhesive qualities, can greatly assist in removing unsanitary materials from the breaths of both parties.

The transparent portion 12 is, as categorized, one in which the resuscitator can easily view the face of the victim, or at least that much of the face as will enable him to locate the mouth of the victim and place the air-permeable filter portion 11 over the victim's mouth. Transparent portion 12 is normally formed from a synthetic film, and I prefer to use a composition marketed under the trademark SARAN, which is polyvinylidene chloride. Transparent portions can be formed from other films, such as synthetic polyester resins and vinyl resins. Stiffening member 13 is, as will be apparent, formed from a material that is relatively stiff yet resilient. I prefer that this material be celluloid, although many other materials, such as organic esters of cellulose, will be suitable. If celluloid is used, the stiffening portion 13 will be translucent or transparent, according to the thickness of the portion. The more transparent it is, the more it will serve as an adjunct to the transparent portion 12 in locating the mouth of the victim.

Figure 2:
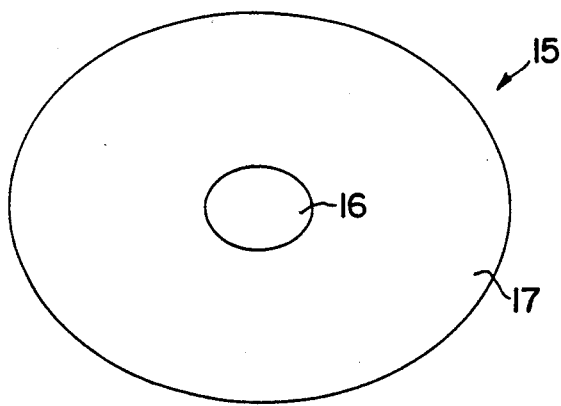
FIG. 2 is a plan view of a two-portion mask according to another embodiment of my invention.
Figure 3:
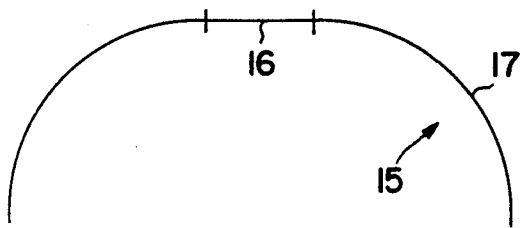
FIG. 3 is a side elevational view of the embodiment of FIG. 2.

Still another embodiment of my invention is shown in FIGS. 2 and 3. Here the mask 15 has a central portion 16, which is substantially the same as the central portion 11 of the mask 10 of FIG. 1. Yet the embodiment of FIGS. 2 and 3 employs a stiffening member 17 which is also transparent. Thus, stiffening member 17 in this embodiment performs the function of both the transparent portion 12 and stiffening portion 13 of the FIG. 1 embodiment. It is most advantageously formed from celluloid or like relatively stiff yet flexible and resilient, transparent material. As shown in FIG. 3, the FIG. 2 mask may be of concavo-convex form, in which it may more easily conform to the shape of the victim's face. This shape is also that preferred for the FIG. 1 embodiment; so long as the mask is generally flexible in order to conform to a victim's facial contour, it may be either flat or concavo-convex.

In use, the mask of FIGS. 1 or 2 is grasped at either stiffening members 13 or 17 and, because portions 12 and 17 are substantially transparent, masks 10 and 15 are located so that central portions 11 and 16 are positioned at the mouth of the victim. Then resuscitation is applied in a normal manner, with the fingers of one hand of the resuscitator closing off the nasal passageway of the victim. By the use of the mask of the present invention, however, the transfer of bacteria, viruses and other unsanitary animal or vegetable matter is greatly inhibited from passing between the mouths of the victim and the resuscitator.

It will be apparent to those of skill in this art that many modifications and alterations may be made in the preferred embodiments of my invention as described hereinbefore. As to all those such obvious modifications and alterations, it is desired that they be included within the purview of my invention, which is to be limited only by the scope, including equivalents, of the following, appended claims.

I claim:

1. A mask adapted to be placed over the mouth of a victim during mouth-to-mouth resuscitation, comprising a substantially opaque, fibrous, air-permeable filter portion having the property of inhibiting the passage of unsanitary materials therethrough, a transparent portion adjacent to said filter portion, said transparent portion comprising a synthetic film surrounding said filter portion but lacking sufficient rigidity to retain its form when handled, and a stiff yet resilient stiffening portion surrounding and maintaining the shape of said transparent portion and said filter portion during use thereof, so that the mask may be grasped by said stiffening portion and visually adjusted through said transparent portion to locate said filter portion over the mouth of the victim.

2. A mask as claimed in claim 1, in which said filter portion is a dry air filter.

3. A mask as claimed in claim 2, in which said dry air filter is composed of a material selected from the group consisting of cotton, cellulose paper, synthetic materials and glass fibers.

4. A mask as claimed in claim 1, in which said filter portion is an impingement filter in which at least one surface of the portion is coated with a liquid to which particles of said unsanitary materials adhere.

5. A mask as claimed in claim 4, in which said liquid is an antiseptic.

6. A mask as claimed in claim 1, in which said film is formed from polyvinylidene chloride.

7. A mask as claimed in claim 1, in which said transparent portion is formed from vinyl resins.

8. A mask as claimed in claim 1, in which said transparent portion is formed from a synthetic polyester resin.

9. A mask as claimed in claim 1, in which said stiffening portion is translucent or transparent.

10. A mask as claimed in claim 1, in which said stiffening portion is formed from celluloid.

11. A mask as claimed in claim 1, in which said stiffening portion is formed from an organic ester of cellulose.

* * * * *